United States Patent [19]
Friese

[11] Patent Number: 5,374,390
[45] Date of Patent: Dec. 20, 1994

[54] PROCESS FOR PRODUCING A LAYER SYSTEM FOR GAS SENSORS

[75] Inventor: Karl-Hermann Friese, Leonberg, Germany

[73] Assignee: Robert Bosch GmbH, Germany

[21] Appl. No.: 64,172

[22] PCT Filed: Dec. 3, 1991

[86] PCT No.: PCT/DE91/00939

§ 371 Date: May 25, 1993

§ 102(e) Date: May 25, 1993

[87] PCT Pub. No.: WO92/12419

PCT Pub. Date: Jul. 23, 1992

[30] Foreign Application Priority Data

Jan. 4, 1991 [DE] Germany .............. 4100107

[51] Int. Cl.$^5$ .............................. B22F 7/04
[52] U.S. Cl. ............................. 419/10; 419/5; 419/19; 419/20; 419/45; 204/424; 204/425; 204/426; 204/421
[58] Field of Search .......... 419/10, 20, 45, 5, 19; 204/424, 425, 426, 427

[56] References Cited

U.S. PATENT DOCUMENTS

| | | | |
|---|---|---|---|
| 3,776,831 | 12/1973 | Roy et al. | 204/195 S |
| 3,989,614 | 11/1976 | Tien | 204/195 S |
| 4,152,234 | 5/1979 | Pollner | 204/195 S |
| 4,170,530 | 10/1979 | Watanabe et al. | 204/195 S |
| 4,265,724 | 5/1981 | Haecker et al. | 204/195 S |
| 4,276,142 | 6/1981 | Topp et al. | 204/195 S |
| 4,283,441 | 8/1981 | Haecker et al. | 427/126.2 |
| 4,296,148 | 10/1981 | Friese | 427/125 |
| 4,299,627 | 11/1981 | Shinohara et al. | 75/206 |
| 4,347,113 | 8/1982 | Fischer et al. | 204/195 S |
| 4,354,912 | 10/1982 | Friese | 204/195 S |
| 4,409,135 | 10/1983 | Akimune et al. | 252/514 |
| 4,847,172 | 7/1989 | Maskalick et al. | 429/30 |
| 5,032,248 | 7/1991 | Kanamaru et al. | 204/429 |

Primary Examiner—Donald N. Walsh
Assistant Examiner—John N. Greaves
Attorney, Agent, or Firm—Spencer, Frank & Schneider

[57] ABSTRACT

A process is proposed which serves to produce layer systems for gas sensors, the electrodes essentially being composed of a finely divided ceramic material and finely divided electron-conducting material. The process comprises adding stabilizer oxides to the electrode material in proportions above those necessary for full stabilization. As a result, a layer system having outstanding mechanical properties and high electrode load carrying capacity is obtained by a simple manufacturing process.

13 Claims, No Drawings

PROCESS FOR PRODUCING A LAYER SYSTEM FOR GAS SENSORS

BACKGROUND OF THE INVENTION

The invention relates to a process in for producing a layer system for gas sensors. German Offenlegungsschrift, or Laid Open Patent Application 29 04 069 discloses layer systems for gas sensors, in particular for lambda probes or polarographic probes, in which an interlayer of fully stabilised zirconium dioxide is formed on a partially stabilised solid electrolyte body before applying metallic or cermet electrodes. This layer sequence makes it possible to exploit the good mechanical strength and high thermal-shock resistance of partially stabilised solid electrolyte material, while at the same time, however, avoiding the disadvantages of these solid electrolyte materials in sensor manufacture. Irreversible transformation of metastable tetragonal $ZrO_2$ into monoclinic $ZrO_2$ produces microstructure damage, initially at the surface of the ceramic and then in the interior of the ceramic as well as a result of crack propagation. Monoclinic zirconium dioxide has, however, also the further disadvantage that it virtually does not conduct $O^{-2}$ ions. The irreversible phase transformation tetragonal to monoclinic zirconium dioxide at the boundary surface between solid electrolyte body and electrodes therefore results in a further disadvantage, namely in a reduction of the electrolyte/electrode/test gas three-phase boundary and, consequently, in an impairment of the electrode function.

The phase transformation of the tetragonal $ZrO_2$, which initially starts at the surface, is substantially suppressed, according to German Offenlegungsschrift, or Laid Open Patent Application 29 04 069, by applying an interlayer of fully stabilised $ZrO_2$ between solid electrolyte body and electrode.

Furthermore, German Offenlegungsschrift, or Laid Open Patent Application 28 52 638 discloses the improvement of the load carrying capacity of gas sensors by using ceramic materials having different sintering activity for the layer system composed of solid electrolyte and cermet electrodes, in which connection the ceramic material for the supporting structure of the cermet electrode should be less sintering-active than the ceramic material of the solid electrolyte.

SUMMARY OF THE INVENTION

The process according to the present invention is characterized by (a) providing a cermet electrode material comprising an ion-conducting ceramic material and an electron conducting material interdispersed with each other; (b) adding an excess amount of a stabilizing substance to the electrode material; (c) applying at least one layer of the electrode material of (b) to an ion-conducting solid ceramic electrolyte optionally containing a stabilizing substance of lower concentration than necessary for full stabilization; and (d) forming a fully stabilized transition region in at least the surface boundary zone of said electrolyte and electrode. The process of the present invention produces gas sensors which comprise an ion-conducting solid electrolyte and an electrode which are essentially ceramic material which forms a supporting structure and from an electroconducting material. It is characterized in that stabilizer oxides and/or compounds which form stabilizer oxides on exposure to high temperature, are added to the electrode material in proportions above those necessary for the full stabilization of the electrode ceramic. The stabilizer oxides at least partially penetrate the surface of the partially stabilized solid electrolyte on applying the cermet electrode and/or during the sintering process and produce fully stabilized transition regions at that point which have increased ion conductivity. This process provides an improved method of producing gas sensors having good mechanical properties and high load carrying capacity of the electrodes. By adding stabilizer oxides to the electrode material in proportions above those necessary for the full stabilisation of the electrode ceramic, a more efficient manufacturing process is provided for the layer system and dispenses with the application of a fully stabilised interlayer.

The solid electrolyte and the ceramic material of the cermet electrode comprise zirconium dioxide and/or thorium oxide and/or hafnium oxide.

The stabiliser oxides which are added to the electrode material diffuse, either as dissolved compounds on applying the cermet electrode and on sintering or as undissolved compounds only on sintering with the partially stabilised solid electrolyte body, into the surface of the latter and produce at that point a fully stabilised transition zone having increased oxygen ion conductivity which, at the same time, substantially prevents the phase transformation of the tetragonal solid electrolyte material. Inside said transition zone, the proportion of stabiliser decreases continuously from the solid electrolyte/electrode boundary surface towards the interior of the solid electrolyte body and is thereby distinguished from the step-like drop in the proportions of stabiliser oxide, such as is achieved by applying an interlayer in accordance with German Offenlegungsschrift, or Laid Open Patent Application 29 04 069. The continuous decrease in the proportions of stabiliser oxide in accordance with the present invention results in lower amounts of stabiliser oxides having to be used, and this is associated with a cost saving and also with improved mechanical properties of the solid electrolyte body. The transition zone is also produced only directly underneath the cermet electrode, i.e. only at the point where the high $O^2$ ion conductivity is needed. In the other surface regions of the solid electrolyte ceramic, on the other hand, the monoclinic $ZrO_2$ transformation zone which increases the strength may be produced.

For the abovementioned reasons, it is advantageous not to increase the proportion of stabiliser oxide substantially above the proportion necessary for full stabilisation. The addition of a total of 15 mol-% of $Y_2O_3$ to a platinum-cermet electrode material made of 60% by volume of platinum to 40% by volume of zirconium dioxide has proved to be particularly advantageous.

According to a further preferred embodiment, it is not stabiliser oxide powders as such which are added to the electrode material, but salts such as, for example, carbonates, acetates, nitrates, chlorides or organometallic compounds which, on exposure to high temperature, during sintering with the solid electrolyte body, form stabiliser oxides.

DESCRIPTION OF THE PREFERRED EMBODIMENTS

The invention will be explained in greater detail by reference to the following examples:

EXAMPLE 1

A platinum-cermet electrode is applied from a suspension containing 60% by volume of platinum/40% by volume of $ZrO_2$ along with 4 mol-% of $Y_2O_3$, to a solid electrolyte ceramic film made of coprecipitated stabilised $ZrO_2$ containing 4 mol-% of $Y_2O_3$, enough free $Y_2O_3$ powder being added in addition for the proportion of yttrium oxide, based on the zirconium dioxide, to be 15 mol-% in total. The suspension is applied in a known manner by spraying-on, brushing-on, rolling-on, immersion, rolling, casting or pressing, dried and then sintered together with the solid electrolyte body in a gas-heated furnace at 1400° C. with a holding time of approximately five hours.

EXAMPLE 2

The layer system is produced as described in Example 1, but instead of 15 mol-% of free $Y_2O_3$ powder, 11 mol-% of $Yb_2O_3$ powder is added to the electrode material.

EXAMPLE 3

Layer system as described in Example 1, but containing 11 mol-% of free $Sc_2O_3$ powder.

EXAMPLE 4

Layer system as described in Example 1, but instead of $Y_2O_3$, a total of 15 mol-% of $Yb_2O_3$ powder is added to the electrode material.

EXAMPLE 5

Process as described in Example 1, but the solid electrolyte body is composed of a $ZrO_2/Y_2O_3$ powder mixture containing 5 mol-% of $Y_2O_3$, and the electrode material contains 60% by volume of platinum to 40% by volume of zirconium dioxide stabilised with 4 mol-% of $Y_2O_3$, and also, additionally, 11 mol-% of free $YO_3$.

It is possible that solid electrolyte and the ceramic material of the cermet electrode comprising zirconium dioxide and/or thorium oxide and/or hafnium oxide.

It is furthermore possible to use other stabiliser oxides, such as, for example, $Y_2O_3$ concentrate which is composed of about 60% by weight of $Y_2O_3$, the remainder being oxides of the rare-earth elements, mainly the heavy rare earths, $Yb_2O_3$ concentrate containing 30% by weight of $Yb_2O_3$, the remainder being mainly oxides of the heavy rare-earth elements, calcium oxide or magnesium oxide. All the layer systems described may carry further layers which are applied in a known manner using plasma or flame-spraying technology.

I claim:

1. A process for producing a layer system for a gas sensor comprising:
   (a) producing a cermet electrode material comprising an ion-conducting ceramic material and an electron conducting material interdispersed with each other;
   (b) adding an excess amount of a stabilizing substance to said electrode material;
   (c) applying at least one layer of the electrode material of (b) to an ion-conducting solid ceramic electrolyte containing a stabilizing substance of lower concentration than necessary for full stabilization;
   (d) forming a fully stabilized transition region in at least the surface boundary zone of said electrolyte and electrode.

2. The process of claim 1, wherein the forming of the fully stabilized transition region of step (d) occurs on application of the cermet electrode material.

3. The process of claim 1 wherein the forming of the fully stabilized transition region of step (d) occurs during sintering.

4. The process of claim 1, wherein the stabilizing substance is a stabilizer oxide or a compound which forms a stabilizer oxide on exposure to high temperature.

5. The process of claim 1, wherein the stabilizing substance in the ceramic region of the electrode material is 8 to 20 mol percent.

6. The process of claim 1, wherein the stabilizing substance in the ceramic region of the electrode material is 10 to 15 mol percent.

7. The process according to claim 1, wherein the ceramic solid electrolyte, the ceramic material of the electrode, or both comprise zirconium dioxide, a thorium oxide, a hafnium oxide, or a mixture of these oxides.

8. The process according to claim 4, wherein the ceramic solid electrolyte, the ceramic material of the electrode, or both comprise zirconium dioxide, a thorium oxide, a hafnium oxide, or a mixture of these oxides.

9. The process according to claim 5, wherein the ceramic solid electrolyte, the ceramic material of the electrode, or both comprise zirconium dioxide, a thorium oxide, a hafnium oxide, or a mixture of these oxides.

10. The process of claim 4 wherein the stabilizing substance is one or a plurality of diyttrium trioxide, diytterbiumtrioxide, discandiumtrioxide, diyttrium trioxide-concentrate, diytterbiumtrioxide-concentrate, a rare earth oxide, calcium oxide or magnesium oxide.

11. The process of claim 4 wherein the compound which forms a stabilizer oxide on exposure to high temperature is a carbonate, an acetate, a nitrate, a chloride or an organometallic compound.

12. The process of claim 1 wherein the solid ceramic electrolyte contains partially stabilized zirconium dioxide and the ceramic material of the electrode contains 15 mol % of diyttrium trioxide as a stabilizing substance.

13. The process of claim 1 wherein the electrode material comprises $ZrO_3/YO_3$ interdispersed with platinum.

* * * * *